United States Patent [19]

Hepburn et al.

[11] Patent Number: 6,123,979
[45] Date of Patent: Sep. 26, 2000

[54] WAX ESTER COMPOSITIONS

[75] Inventors: Paul Hepburn; Paul Thomas Quinlan; Kevin Warren Smith; James Vincent Watts, all of Sharnbrook, United Kingdom; Reginaldus Petrus J van der Wielen, Wormerveer, Netherlands

[73] Assignee: Unilever Patent Holdings BV, Vlaardingen, Netherlands

[21] Appl. No.: 09/177,381

[22] Filed: Oct. 23, 1998

[30] Foreign Application Priority Data

Oct. 24, 1997 [EP] European Pat. Off. ............. 97308500

[51] Int. Cl.$^7$ ................................................ A23D 9/007
[52] U.S. Cl. .......................... 426/611; 426/601; 554/223; 554/224
[58] Field of Search ..................... 426/611, 601; 554/223, 224; 560/4; 435/134

[56] References Cited

U.S. PATENT DOCUMENTS

| | | | |
|---|---|---|---|
| 4,152,278 | 5/1979 | Bell | 252/565 |
| 4,315,040 | 2/1982 | Heine et al. | 426/609 |
| 4,510,093 | 4/1985 | Hulsmann | 260/410.9 N |
| 4,565,646 | 1/1986 | Hofeditz | 252/309 |
| 4,826,767 | 5/1989 | Hansen | 435/134 |
| 4,880,657 | 11/1989 | Guffey et al. | 426/601 |
| 4,960,602 | 10/1990 | Talkington et al. | 426/534 |
| 5,021,256 | 6/1991 | Guffey et al. | 426/601 |
| 5,053,169 | 10/1991 | Price | 260/428 |
| 5,338,564 | 8/1994 | Meyer et al. | 426/612 |
| 5,474,604 | 12/1995 | Demmering | 106/38.24 |
| 5,496,565 | 3/1996 | Heinze | 424/502 |
| 5,608,122 | 3/1997 | Buchold | 568/885 |
| 5,968,530 | 10/1999 | Arquette | 424/401 |

FOREIGN PATENT DOCUMENTS

| | | |
|---|---|---|
| 0 290 421 | 11/1988 | European Pat. Off. . |
| WO 95/28847 | 11/1997 | WIPO . |

OTHER PUBLICATIONS

Ergan et al, JAOCS, vol. 68, No. 1, (Jan. 1991).
Sessa, J. Sci. Food Agric., 72:295–298 (1996).

*Primary Examiner*—Carolyn Paden
*Attorney, Agent, or Firm*—Pillsbury Madison & Sutron LLP

[57] ABSTRACT

Blends of wax-esters with beneficial health properties comprise: ≧ two different wax-esters in amounts of 5–95% and each having m.pt −10° C. to 80° C. blend displaying m.pt: 15 to 45% while >80 wt % of wax-esters in blend have m.pt 20 to 60° C.; wax-esters derived from linear alcohols and linear carboxyl acids either of them having ≧8 C-atoms.

20 Claims, No Drawings

WAX ESTER COMPOSITIONS

FIELD OF THE INVENTION

The invention relates to wax esters which are useful as healthy replacements for fats.

DESCRIPTION OF RELATED ART

Food products often contain fats. The consequence of the presence of fats in food products is that the caloric value of the food products is very high. Moreover fats, in particular saturated and trans fats are considered not being healthy. Therefore a trend exists to replace the fats of the food products by other components that are considered to be healthier. Examples of such fat replacers are eg denatured proteins with a small particle size. Fat replacers however should not only reduce the caloric content of the products but should also retain the fatty impression and the mouthfeel of fats. Further the fat replacers should be able to take over the structuring properties of fats. These requirements are however not fulfilled by the use of these denatured proteins. Other known fat replacers are derived from sugars and contain a high number of fatty acid residues. Although these fat replacers imitate the fatty impression very well they have other disadvantages such as an anal leakage problem when applied in the amounts necessary for fat replacers.

It will not have to be explained that fat replacers should also be safe for use in food products. So compounds that display detrimental properties when consumed are not applicable as fat replacer.

According to WO 95/28847 a number of wax esters can be applied in food products that have an emulsified fat phase. The wax esters act here as structuring components and are used in amounts of 1.5–6 wt % on fat phase. Wax esters that can be applied are bees wax, carnauba wax, candelilla wax, spermaceti wax, Japan wax, jojoba oil and hardened jojoba oil. In this reference it is not indicated that these wax esters can also be used as fat replacer or to reduce the caloric content of the food product. This can be explained by our finding that these wax esters, in particular jojoba oil have a detrimental effect in the form of body weight reduction/reduced growth, reduced food and water consumption and toxicological significant changes in several blood clinical chemistry parameters, such as plasma enzyme activities. Also histopathological changes in the mesenteric nodes and jejunum were observed when administrating higher proportions of these wax esters. On basis of above observations it was very unlikely that wax esters could be found that did not have the above detrimental properties.

Still we performed a study to find out whether wax esters could be found that could be used successfully in food products as fat replacer but that do not display the disadvantages of the wax esters from the prior art. This study resulted in the finding of novel wax ester blends that perform very well in fat based food products, that do not display detrimental health aspects and that can be used as fat replacers and to reduce the caloric intake of food products based on them.

SUMMARY OF THE INVENTION

Therefore our invention concerns in the first instance a blend of at least two different wax-esters, wherein the individual wax-esters each have a melting point between −10 and 80° C. while the blend displays a melting point between 15 and 45° C. and at least 80 wt % of the wax-esters, present in the blend has a melting point between 20 and 60° C., while the wax-esters are derived from linear alcohols and linear carboxylic acids each having an even number of carbon atoms, while either the alcohol or the acid residue or both have at least 8 C atoms, preferably the acid residue comprises 12–24 C-atoms, most preferably 16–22 C-atoms and wherein the blend comprises at least two wax esters each in amounts of 5–95 wt %.

DETAILED DESCRIPTION OF THE INVENTION

The wax esters can contain different fatty acid residues and different alcohol residues. Preferred wax ester blends however comprise wax esters wherein at least one of the wax-esters is derived from either a saturated or unsaturated carboxylic acid with at least 16 C atoms or from a saturated or unsaturated alcohol with at least 8 C atoms preferably at least 16 C atoms or from both simultaneously.

The most preferred wax esters are derived from saturated carboxylic acids with at least 18 C atoms, preferably being stearic acid. These wax esters give the best caloric reduction.

The carboxylic acids can thus be saturated but very useful wax esters are also obtained if the carboxylic residue is mono- or poly-, in particular diunsaturated and preferably have at least 18 C atoms, preferably being oleic acid and/or linoleic acid. Very beneficial wax esters are obtained if the carboxylic acid residues are long chain polyunsaturated fatty acids, such as arachidonic acid, EPA or DHA. Using these wax esters will incorporate the well known beneficial health aspects from these essential fatty acids in the food product.

The alcohol residue of our wax esters can be selected from saturated alcohols with at least 2, preferably at least 8, more preferably at least 12 and most preferably at least 18 C atoms.

Very beneficial combinations are obtained if the blend comprises at least one wax-ester derived from a saturated long chain alcohol, having at least 8, preferably at least 12 C atoms, more preferably at least 18 C atoms and an unsaturated carboxylic acid with at least 8, preferably at least 12 C atoms, more preferably at least 18 C atoms.

A main advantage of our novel blends is, that the trans fatty acid content is low, ie below 5 wt % and preferably below 2 wt %.

Our novel blends of wax esters are applied as fat replacer and are therefore in general used in combination with triglycerides. Part of the invention thus also are blends of wax-esters and triglycerides, which blends contain at least 20 wt %, preferably 25–95 wt % most preferably 30–90 wt % of the blend of wax-esters.

These blends preferably comprise vegetable triglycerides or fish derived triglycerides selected from the group consisting of: liquid oils, fractions of hardened liquid oils, hardened liquid oils, cocoa butter, cocoa butter equivalents, palm oil, fractions of palm oil, fish oils, fish oil fractions, hardened fish oils, fractions of hardened fish oils, enzymically made equivalents of the oils mentioned and mixtures of one or more of the oils mentioned. Also single cell oils can be used.

In order to be useful in food applications wherein the fat phase is used for structuring purposes it is advantageous if our blends of wax esters and triglycerides display an N-value-profile (NMR pulse, non stabilised) of: N20=5–80, preferably 15–60 N30=2–60, preferably 5–45 N35=<20, preferably <10, most preferably <5 The N values were measured after subjecting the blend to the following temperature regime: melt at 80° C., cool to 0° C. and keep at 0° C. for 1 hr, warm up to measurement temperature and keep it there for half an hour and measure the N value by NMR pulse.

Although in principle our food products could be completely fat free, we found that the best results were obtained if our food compositions comprise a lipid phase, which is present for at least 10 wt % and which lipid phase comprises at least 20 wt % of a blend of wax-esters, preferably a blend. The amount of lipid phase is preferably at least 20 wt %, more preferably at least 30 wt % and most preferably at least 35 wt % based on food composition.

Examples of food products that can be made by using our blends of wax esters are:

i) a spread, preferably having a continuous fat phase with 10–90 wt % fat content and 90–10 wt % water
ii) a confectionery product
iii) ice creams, ice cream coatings, inclusions for ice creams
iv) dressings, mayonnaise, sauces
v) bakery fats
vi) cheese According to another embodiment of our invention we use our wax esters or blends of wax esters and triglycerides in food products to structure the products and to lower the caloric content of the food product.

Part of our invention is also a process for the preparation of our blends of wax-esters. Although these wax-esters can be made by a chemical esterification of an alcohol and a fatty acid, we prefer to apply an enzymic conversion of fatty acids with preferably at least 8 C-atoms and aliphatic alcohols with at least 2 C-atoms. For this conversion any enzymic esterification catalyst can be applied.

EXAMPLES

1 Preparation of Stearyl Oleate

Preparation

Stearyl alcohol (477 g) and oleic acid (523 g) were placed in a 2-liter rotary evaporator flask with 2% Mucor miehei lipase immobilised on Duolite (SP392 ex. Novo). The mixture was heated to 65° C. in a waterbath and vacuum was applied to remove water generated during the reaction. Stirring was achieved by rotating the flask using a rotary evaporator. The reaction was allowed to proceed for four hours.

The above procedure was repeated twice (i.e. a total of three batches were prepared).

The combined reaction products were heated to a temperature of 120° C. by steam in a stirred jacketed vessel. A calculated amount of sodium hydroxide solution was added to the vessel in order to neutralise free fatty acid. The sodium soap formed was run off from the bottom of the vessel. To remove final traces of soap, the oil was washed several times with boiling water, the soap/water mixture being run off from the bottom of the vessel after settling.

The remaining reaction product was dried using a rotary evaporator under vacuum at a temperature of 90° C. The dried wax product was then bleached by stirring with C300 bleaching earth for 30 minutes at a temperature of 90° C. followed by filtration.

Analysis

Fatty acids were analyzed by GC of the methyl esters while fatty alcohols were analyzed by GC without further preparation.

| % | C16:0 | C18:0 | C18:1 | C18:2 | C20.1 |
|---|---|---|---|---|---|
| Oleic acid | 0.7 | 2.6 | 90.7 | 5.6 | 0.3 |
| Stearyl alcohol | | >99 | | | |

Lipid classes were determined by HPLC:

| Component | % |
|---|---|
| Alcohol | 0.1 |
| Wax Ester | >99 |

Separation according to molecular weight was carried out by GC of the wax esters:

| Carbon Number | C34 | C36 | C38 |
|---|---|---|---|
| Stearyl Oleate | 1.2 | 98.3 | 0.5 |

N-values were measured:

| Wax Ester | N20 | N25 | N30 | N32.5 | N35 |
|---|---|---|---|---|---|
| Stearyl Oleate | 94.2 | 0 | | | |

2. Preparation of Behenyl Linoleate/Oleate

Preparation

Following the method for stearyl oleate according to example 1, behenyl alcohol (524 g) was reacted with fatty acids produced by hydrolysis of sunflower oil (476 g).

After bleaching the resultant wax ester was heated to 35° C. and centrifuged at 3000 G for 30 minutes at 3100 rpm before decanting off the behenyl linoleate/oleate mixture. This removed much of the saturated wax esters.

Analysis

Fatty acids were analyzed by GC of the methyl esters while fatty alcohols were analyzed by GC without further preparation.

| % | C14:0 | C16:0 | C16:1 | C18:0 | C18:1 | C18:2 | C18:3 | C20:0 | C20.1 | C22:0 |
|---|---|---|---|---|---|---|---|---|---|---|
| Sunflower oil hydrolysate | 0.3 | 4.4 | 0.2 | 1.5 | 27.3 | 65.4 | 0.5 | 0.1 | 0.3 | 0 |
| Behenyl alcohol | | | | | | | | | | >99 |

Lipid classes were determined by HPLC and show the presence of glycerides due to incomplete hydrolysis of the sunflower oil:

| Component | % |
|---|---|
| Alcohol | 1.0 |
| Diglyceride | 0.4 |
| Triglyceride | 0.6 |
| Monoglyceride/Other | 0.8 |
| Wax Ester | 97.2 |

Separation according to molecular weight was carried out by GC of the wax esters:

| Carbon Number | 36 | 38 | 40 | 42 | 44 |
|---|---|---|---|---|---|
| Behenyl Linoleate/Oleate | 2.4 | 8.6 | 86.3 | 1.8 | 0.9 |

| Fatty acid methyl esters were prepared from the wax ester and analyzed by GC: | | | | | | | | | | |
|---|---|---|---|---|---|---|---|---|---|---|
| Acid | C14:0 | C16:0 | C16:1 | C18:0 | C18:1 | C18:2 | C18:3 | C20:0 | C20:1 | C22:0 |
| Behenyl Linoleate/Oleate | 0.5 | 2.1 | 0.2 | 0.4 | 29.2 | 67.4 | 0.3 | 0 | 0 | 0 |

| 5 N-values were measured unstabilised: | | | | | |
|---|---|---|---|---|---|
| Wax Ester | N20 | N25 | N30 | N32.5 | N35 |
| Behenyl Linoleate/Oleate | 85.1 | 84.2 | 79.9 | 52.8 | 0 |

3. Preparation of Chocolate Coating

The following recipe was applied:

| | |
|---|---|
| cocoa powder (10/12) | 16 wt % |
| skimm. milk powder | 8 |
| Icing sugar | 55 |
| Blend of: olein fraction of behenic esters of sunflower acids (cf: ex. 2) and sunflower oil (ratio: 80:20) | 21 |
| Lecithin | 0.2 |

This mixture was treated on a Buhler triple roller. The resulting product was conched for 5 hrs at 50–60° C., using 88 wt % of the paste resulting from the Buhler roller and 12 wt % of the same olein-fraction of behenic esters of sunflower acids and sunflower oil.

Rubber corks were coated with the conched mixture. The chocolate solidified quickly and did not bloom (stored 70 days at 20° C. or 6 weeks at 25° C.).

What is claimed is:

1. Blend of at least two different wax-esters each present in amounts of 5–95 wt %, said individual wax-esters each having a melting point between −10 and 80° C. while the blend displays a melting point between 15 and 45° C. and at least 80 wt % of the wax-esters present in the blend having a melting point between 20 and 60° C., the wax-esters being derived from a saturated linear alcohol of at least 8 C atoms and a linear mono- or di-unsaturated carboxylic acid of at least 18 C atoms, the alcohol and acid each having an even number of carbon atoms.

2. Blend according to claim 1 wherein-the acid is at least one member of the group consisting of oleic acid and linoleic acid.

3. Blend of at least two different wax-esters each present in amounts of 5–95 wt %, said individual wax-esters each having a melting point between −10 and 80° C. while the blend displays a melting point between 15 and 45° C. and at least 80 wt % of the wax-esters present in the blend having a melting point between 20 and 60° C., the wax-esters being derived from a saturated or unsaturated linear alcohol of at least 8 C atoms and a linear polyunsaturated carboxylic acid with at least 18 C atoms and having at least 3 unsaturations.

4. Blend according to claim 1 or claim 3, wherein the wax-esters contain a saturated alcohol residue with at least 12 C atoms.

5. Blend according to claim 4 wherein the saturated alcohol residue has at least 18 C atoms.

6. Blend according to claim 1 or claim 3, wherein the blend comprises at least one wax-ester derived from a saturated long chain alcohol, having at least 12 C atoms.

7. Blending according to claim 6 wherein the saturated long chain alcohol has at least 18 C atoms.

8. Blend according to claim 1 or claim 3, wherein the trans fatty acid content is less than 5 wt %.

9. Blend according to claim 8 wherein the trans fatty acid content is less than 2 wt %.

10. Blends of wax-esters and triglycerides, which blends contain at least 20 wt % of the blend of wax-esters according to claim 1 or claim 3.

11. Blend of wax-esters and triglycerides according to claim 10, wherein the blend comprises vegetable triglycerides selected from the group consisting of: liquid oils, fractions of hardened liquid oils, hardened liquid oils, cocoa butter, cocoa butter equivalents, palm oil, fractions of palm oil, fish oils, fish oil fractions, hardened fish oils, fractions of hardened fish oils, enzymically made equivalents of the oils mentioned and mixtures of one or more of the oils mentioned.

12. Blend according to claim 10 comprising 30–90 wt % of said blend of wax-esters.

13. Blend according to claim 3 wherein the acid is EPA or DHA.

14. Blend of wax-esters and triglycerides which blends contain at least 20 wt % of a blend of at least two different wax-esters each present in amounts of 5–95 wt %, said individual wax-esters each having a melting point between −10 and 80° C. while the blend displays a melting point between 15 and 45° C. and at least 80 wt % of the wax-esters present in the blend having a melting point between 20 and 60° C., the wax-esters being derived from (1) a saturated or unsaturated linear alcohol of at least 8 C atoms and a linear mono- or di-unsaturated carboxylic acid of at least 18 C atoms, the alcohol and acid each having an even number of carbon atoms or (2) a saturated or unsaturated linear alcohol of at least 8 C atoms and a linear polyunsaturated carboxylic acid with at least 18 C atoms and having at least 3 unsaturations, said triglycerides being vegetable triglycerides selected from the group consisting of: liquid oils, fractions of hardened liquid oils, hardened liquid oils, cocoa butter, cocoa butter equivalents, palm oil, fractions of palm oil, fish oils, fish oil fractions, hardened fish oils, fractions of hardened fish oils, enzymically made equivalents of the oils mentioned and mixtures of one or more of the oils mentioned, said blend displaying an N-value profile (NMR pulse, non-stabilised) of:

$N20 = 5–80$, $N30 = 2–60$ and $N35 = <20$.

15. Blend according to claim 14 which displays an N-value profile as follows:

$N20$ of 15–60

$N30$ of 5–45 and $N35$ of <5.

16. Food composition comprising a lipid phase, which is present for at least 10 wt % and which lipid phase comprises at least 20 wt % of a blend of wax-esters, said blend comprising at least two different wax-esters each present in amounts of 5–95 wt %, said individual wax-esters each having a melting point between −10 and 80° C. while the blend displays a melting point between 15 and 45° C. and at least 80 wt % of the wax-esters present in the blend having a melting point between 20 and 60° C., the wax-esters being derived from (1) a saturated or unsaturated linear alcohol of at least 8 C atoms and a linear mono- or di-unsaturated carboxylic acid of at least 18 C atoms, the alcohol and acid each having an even number of carbon atoms or (2) a saturated or unsaturated linear alcohol of at least 8 C atoms and a linear polyunsaturated carboxylic acid with at least 18 C atoms and having at least 3 unsaturations.

17. Food composition according to claim 16, wherein the food composition comprises at least 20 wt % of lipid phase.

18. Food compositions according to claim 17, wherein the food is selected from the group consisting of:

i) a spread ii) a confectionery product iii) ice creams, ice cream coatings, inclusions for ice creams iv) dressings, mayonnaise, sauces v) bakery fats vi) cheese.

19. Food composition according to claim 18 wherein the blend functions as a structuring component with a low caloric content.

20. Process for the preparation of blends of wax-esters of at least two different wax-esters each present in amounts of 5–95 wt %, said individual wax-esters each having a melting point between −10 and 80° C. while the blend displays a melting point between 15 and 45° C. and at least 80 wt % of the wax-esters present in the blend having a melting point between 20 and 60° C., the wax-esters being derived from (1) a saturated or unsaturated linear alcohol of at least 8 C atoms and a linear mono- or di-unsaturated carboxylic acid of at least 18 C atoms, the alcohol and acid each having an even number of carbon atoms or (2) a saturated or unsaturated linear alcohol of at least 8 C atoms and a linear polyunsaturated carboxylic acid with at least 18 C atoms and having at least 3 unsaturations which comprise enzymically converting the fatty acid of at least 18 C-atoms and said alcohol of at least 8 C-atoms to said wax-ester blend.

* * * * *